United States Patent [19]
Borodulin et al.

[11] Patent Number: 5,868,662
[45] Date of Patent: Feb. 9, 1999

[54] METHOD FOR IMPROVING OBSERVATION CONDITIONS IN URETHRA AND A CYSTOSCOPE FOR CARRYING OUT THE METHOD

[75] Inventors: German Borodulin, San Francisco; Gary E. Leach, Rowland Heights; Alexander Shkolnik, San Carlos, all of Calif.

[73] Assignee: Advanced Urological Developments

[21] Appl. No.: 876,223

[22] Filed: Jun. 16, 1997

[51] Int. Cl.$^6$ ........................................................ A61B 1/00
[52] U.S. Cl. ............................ 600/105; 600/135; 600/116
[58] Field of Search ................................... 600/105, 115, 600/116, 135; 604/96, 99, 102, 103

[56] References Cited

U.S. PATENT DOCUMENTS

| | | | |
|---|---|---|---|
| 5,030,227 | 7/1991 | Rosenbluth et al. | 600/116 X |
| 5,188,596 | 2/1993 | Condon et al. | 600/116 X |
| 5,263,962 | 11/1993 | Johnson et al. | 600/116 X |

*Primary Examiner*—Beverly M. Flanagan

[57] ABSTRACT

A cystoscope of the invention comprises a main portion (10) and a tubular sheath (12, 110) that carries on its distal end a balloon (22, 114, 214) inflatable from the outer side of the cystoscope for spreading apart the prostate lobes in the prostatic part of the urethra and thus improving conditions for observation and operation on the prostate. The invention also provides a cystoscope convertible into a resectoscope which consists of a sheath (12, 110) and an outer sleeve (112), slidingly guided over the sheath. On the outer side of its distal portion, the sliding outer sleeve (112) carries an inflatable balloon (114) which is connected to an air-feed tube (118) located inside the sheath. The outer sleeve is connected to an inner sleeve (116) which slides inside the sheath. The distal end face (110*b*) of the sheath is inclined at an acute angle to accommodate the inclined optical portion of the cystoscope, whereas the distal end face (116*a*) of the inner sleeve is arranged substantially at 90° to the longitudinal direction of the instrument to define the resectoscopic end of the instrument. Thus, the instrument is inserted once and can be used both for observation and operation by shifting the inner sleeve forward or backward and replacing the optical system, thus converting the instrument into a resectoscope or a cystoscope. At the same, time, by supplying air into the balloon (114) via the air-feed tube (118), which also functions as a pusher for the moveable part of the instrument, it is possible to inflate the balloon (114) and thus to move the prostate lobes apart and to improve observation conditions in the operation site.

6 Claims, 3 Drawing Sheets

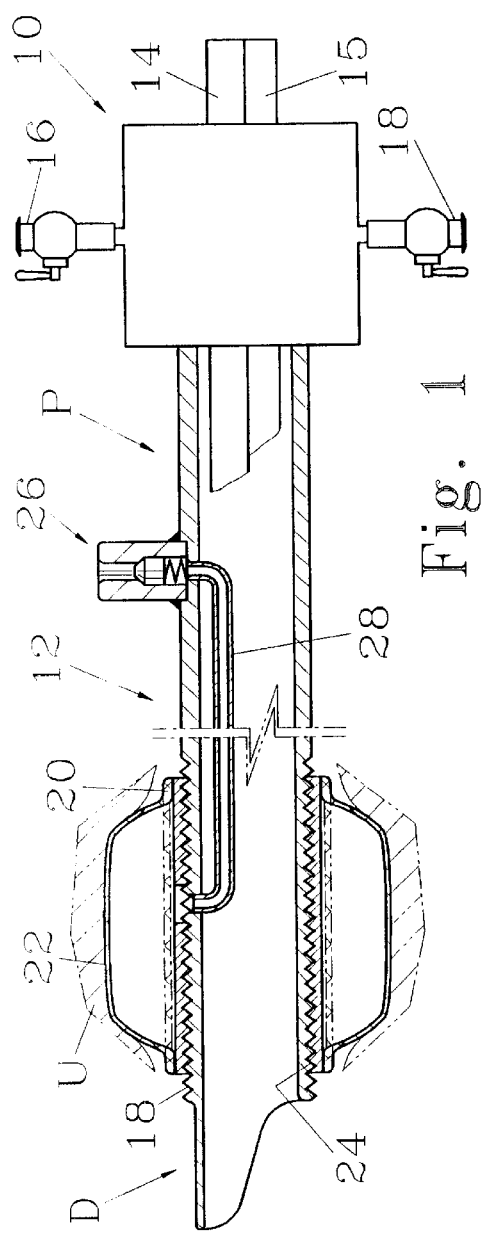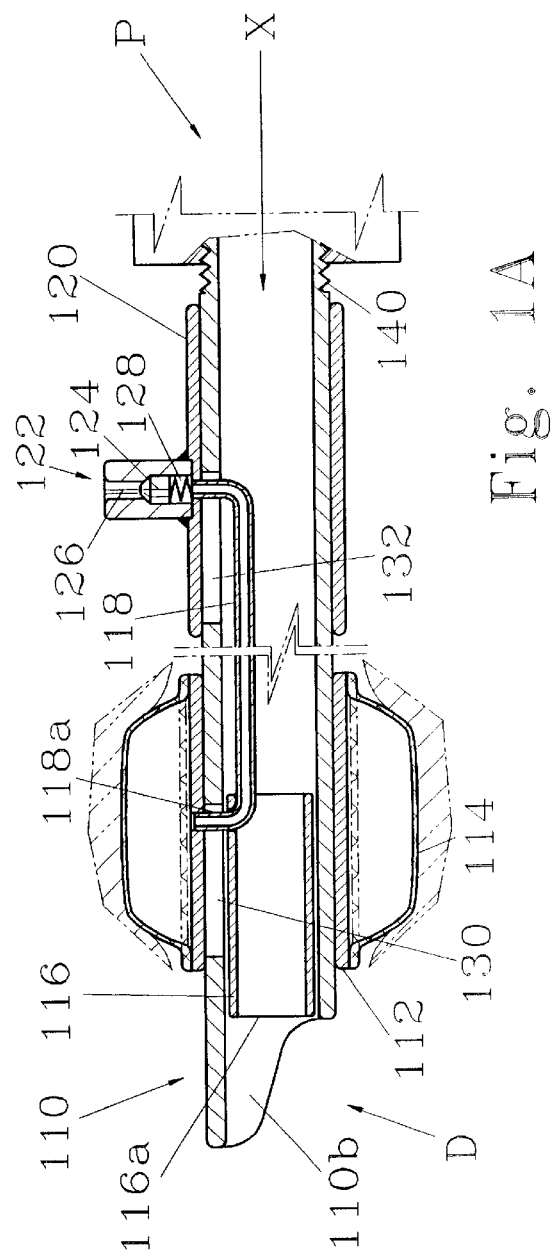

METHOD FOR IMPROVING OBSERVATION CONDITIONS IN URETHRA AND A CYSTOSCOPE FOR CARRYING OUT THE METHOD

FIELD OF THE INVENTION

The present invention relates to the field of urology, particularly to a urological instrument for examination and treatment procedures performed on urethra and urinary bladder, such as transurethral prostatectomy, and the like. More specifically, the invention relates to a method for improving observation conditions in urethra and to a cystoscope for carrying out the method.

DESCRIPTION OF THE PRIOR ART

Prostatectomy is an operation of removal of benign tumor of the prostate gland. This operation can be carried out by different methods such as with the use of loops (resection of the tissue of the enlarged prostate gland is performed by means of a loop-like electrode), rollers, or laser (vaporization of the enlarged portion of the prostate gland by ablation, i.e., an increase of the temperature of the tissue up to more than 100° C.).

Prior to operation, the prostatic part of the urethra and the urinary bladder should be visually examined. The urinary bladder is observed by means of a cystoscope where the optical end of the cystoscope may be inclined at different acute angles to the axial direction of the instrument. On the other hand, the prostatic part of the urethra should be examined and the operation itself should be performed with the use of a resectoscope the optical end of which is arranged substantially at 90° to the axial direction of the instrument. Thus, two different instruments should be inserted into and/or through the urethra. It is known that each additional insertion of the instrument into the urethra increases the risk of complications.

It is also known that in prostatectomy the operation site is very narrow and obscured due to radially inwardly directed forces developed by the enlarged prostate which constricts the prostatic part of the urethra. Therefore the operation is difficult to perform, especially if bleeding in the operation site is present.

OBJECTS OF THE INVENTION

It is an object of the present invention to provide a cystoscope with an inflatable balloon on its distal end for improving operation and observation conditions in the urethra. Another object of the invention is to provide a cystoscope convertable into resectoscope which allows observation of the urinary bladder and of the prostatic part of the urethra and which also allows to perform the prostatectomy itself with one insertion of the instrument into the patient's urethra. Still another object of the invention is to provide the instrument of the aforementioned type which is capable of moving the prostate lobes apart and thus of improving observation and operation conditions for prostatectomy.

BRIEF DESCRIPTION OF THE DRAWINGS

FIG. 1 is a longitudinal sectional view of a cystoscope of the present invention with a disposable balloon.

FIG. 1a is a longitudinal sectional view of a cystoscope of the present invention with a disposable sheath together with the balloon.

SUMMARY OF THE INVENTION

Figure 2:
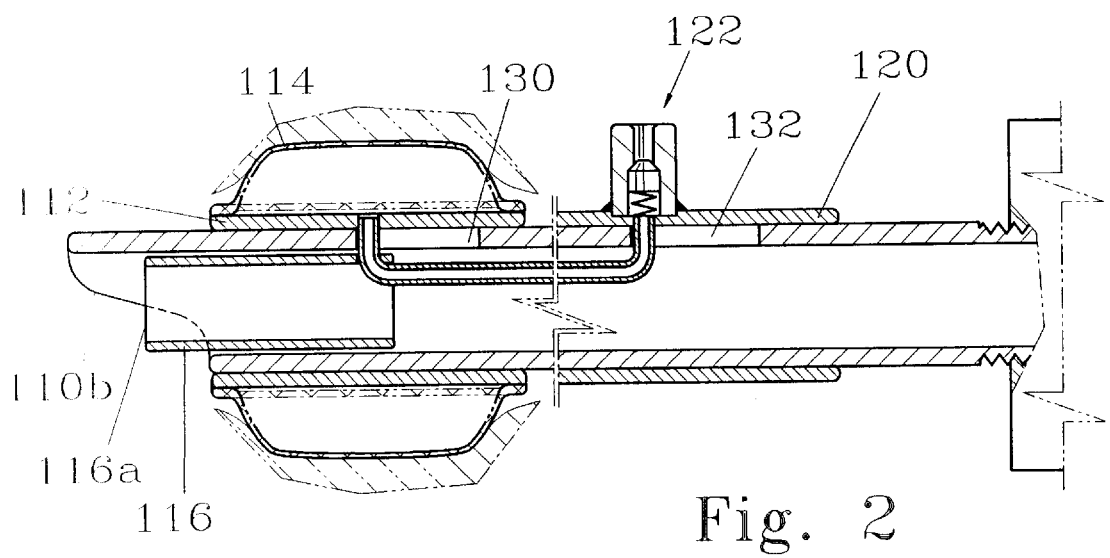
FIG. 2 is a fragmental view of the distal end of the cystoscope of FIG. 1a after conversion into resectoscope.

A cystoscope of the invention comprises a main portion and a tubular sheath that carries on its distal end a balloon inflatable from the outer side of the cystoscope for spreading apart the prostate lobes in the prostatic part of the urethra and thus improving conditions for observation and operation on the prostate. The invention also provides a cystoscope convertable into a resectoscope which consists of a sheath and an outer sleeve slidingly guided over the sheath. On the outer side of its distal portion, the sliding outer sleeve carries an inflatable balloon which is connected to an air-feed tube located inside the sheath. The inner side of the outer sleeve is connected to an inner sleeve which slides inside the sheath. The distal end face of the sheath is inclined at an acute angle to accommodate the inclined optical portion of the cystoscope, whereas the distal end face of the inner sleeve is arranged substantially at 90° to the longitudinal direction of the instrument to define the resectoscopic end of the instrument. Thus, the instrument is inserted once and can be used both for observation and operation by shifting the inner sleeve forward or backward and replacing the optical system, thus converting the instrument into a resectoscope or a cystoscope. At the same, time, by supplying air into the balloon via the air-feed tube, which also functions as a pusher for the sliding part of the instrument, it is possible to inflate the balloon and thus to move the prostate lobes apart and to improve observation conditions in the operation site.

DETAILED DESCRIPTION OF THE PREFERRED EMBODIMENT OF THE INVENTION

The invention will be now described in detail with reference to the accompanying drawings wherein FIG. 1 is a longitudinal sectional view of a cystoscope of the invention which is equipped with a disposable inflatable balloon.

As shown in FIG. 1, in general the cystoscope of the present invention is similar to a conventional cystoscope and consists of a main portion 10 and a tubular sheath 12. The main portion 10 is equipped with conventional devices such as pipe unions 16 and 18, e.g., for the supply of washing and cooling liquids, and channels for insertion of guide pipes 14 and 15 for an optical system and for operating tools such as laser fiber, etc. (not shown). Since the main part 10 is conventional and is beyond the scope of the present invention, it will not be further described.

A distinguishing feature of the cystoscope of the invention is that the distal end D of tubular sheath 12 has a male thread 18 for screwing a support 20 of an inflatable balloon 22. For this purpose, balloon support 20 has a mating female thread 24. This feature is important since the cystoscope itself is a non-disposable instrument designed for multiple use, and the balloon must be disposed after each operation and replaced by a new disposable and sterile balloon.

The proximal end P of tubular sheath 12 supports a check valve 26 which is connected to balloon 22 via a tube 28 that extends along and inside tubular sheath 12.

Prior to operation, a disposable sterile balloon assembly 20, 22 is screwed onto thread 18 of sheath 12.

In operation, e.g., in laser prostatectomy, the cystoscope of FIG. 1 is inserted into the urethra U with observation by means of the optical system (not shown) inserted into guide tube 14, and its distal end D is positioned so that balloon 22 occurs in the prostatic part of the urethra beyond the boundaries of the external sphincter. Balloon 22 is inflated via check valve 26, e.g., by means of syringe (not shown). The inflation of the balloon moves the lobes of the prostatic gland (not shown) apart, thus improving observation and operating conditions.

FIG. 1a shows a cystoscope convertable into a resectoscope.

As shown in this drawing, the combined cystoresectoscope of the invention (hereinafter referred to as "instrument") consists of a sheath 110 which has an axial direction X and slidingly supports on its distal end D an outer tubular portion 112. The latter supports on its outer side an inflatable balloon 114 made of an inflatable medically-acceptable rubber or plastic. The ends of balloon 114 are sealed against the surface of outer tubular portion 112, e.g., by thermal welding. The inflatable portion should be as close to the distal end as possible.

The inner side of outer tubular portion 112 is connected to an inner sleeve 116 which is slidingly installed inside sheath 110. This connection is achieved by means of a bent end 118a of an air-feed tube 118 which passes through inner sleeve 116 to balloon 114. Tube 118 extends in the rearward direction of the instrument inside main tube 110 along its inner wall. It is sufficiently rigid to function as a pusher for the moveable portion to which it is connected, i.e., to slidable outer tubular portion 112 and inner sleeve 116.

At the proximal end P of the instrument, the other end of air-feed tube 116 is connected to a slider 120 which slides over the outer surface of the proximal end of sheath 110 and contains a check valve 122. The latter has a spring-loaded valve element 124 which normally keeps an air inlet opening 126 in a closed state under the effect of a spring 128.

A slot 130 is provided in the distal portion and a slot 132 is provided in the proximal portion of sheath 110 to allow shifting of tube 118, outer tubular portion 112, and inner sleeve 116 with respect to sheath 110.

The distal end of main tube 110 has an elongated cut out 110b and is inclined at an acute angle, e.g., 45° to the axial direction X of the instrument to accommodate the inclined optical portion (not shown) of the cystoscope, whereas the distal end 116a of inner sleeve 116 is arranged substantially at 90° to the longitudinal direction of the instrument to define the resectoscopic end of the instrument.

In this embodiment, proximal end P of sheath 110 may have an outer thread 140, so that entire sheath portion 110 of FIG. 1A together with balloon 114 and the moveable parts can be replaced by the unit of a different size or can be used as a disposable unit for connection to a stationary part of a conventional resectoscope (not shown).

Figure 3:
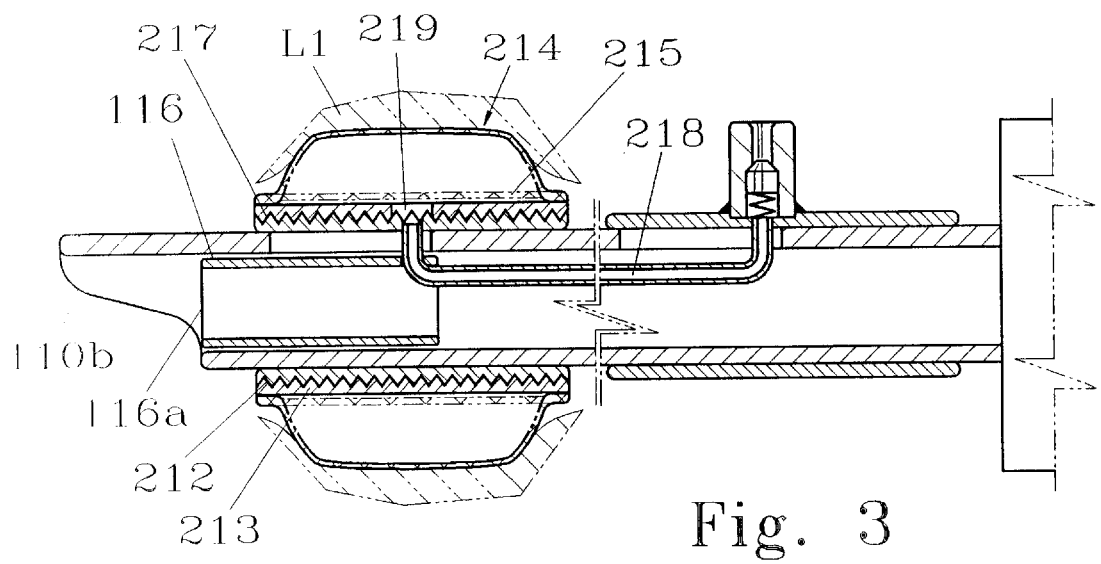
FIG. 3 is a fragmental view of the distal portion of the cystoscope in accordance with another embodiment of the device of FIG. 1a in which a balloon portion is disposable and can be connected by screwing onto the outer tubular portion of the instrument.

FIG. 3 is a fragmental view of the distal portion of the cystoscope convertable into resectoscope and provided with a disposable balloon which can be connected by screwing to the outer tubular portion of the instrument. The instrument of this embodiment is essentially the same as the one described with reference to FIG. 1, with the exception that outer tubular portion 212 has a thread 213, so that a support sleeve 215 of a disposable balloon 214 which also has a thread 217 can be screwed onto outer tubular portion 212 to a position in which an opening 219 of the balloon is aligned with the open end of air-feed tube 218. This is achieved by selecting the lengths of the mating threaded portions on outer tubular portion 212 and the disposable balloon so that when inner thread 217 of the disposable balloon is screwed onto outer thread 213 of outer tubular portion 212, opening 219 and the end of tube 218 are aligned. To compensate for manufacturing inaccuracies, opening 219 may be wider than the diameter of tube 218 and may extend in a circumferential direction. The rest of the instrument of FIG. 3 is identical to the one of FIG. 1.

The convertable instruments of FIGS. 1a and 3 are identical in operation and are used as follows.

After the patient is prepared to the procedure in accordance with the specific requirements for the operation, first the instrument is used as a urethroscope. For this purpose, the moveable portion which consists of an outer tubular portion 112 and inner sleeve 116 (FIG. 1A) is shifted forward via rigid air-supply tube 118 by pushing slider 120 forward toward the distal end D of the instrument along main tubular body 110. As a result, the instrument will be converted into a urethroscope because the distal end face 116a of inner sleeve 116 will assume a position of the type shown in FIG. 3. Now the optical lens system (not shown) with the lens plane perpendicular to the axial direction of the instrument is inserted into the respective guide tube (not shown). If necessary, the 90° optics may inserted into this tube prior to the conversion of the instrument.

The urethroscope is inserted into the urethra U and is moved forward for the observation of the patient's urethra. After the instrument has passed through the urethra into the urinary bladder (not shown), the inclined optical lens system is removed, and the instrument is converted into a cystoscope by shifting outer tubular portion 112 and inner sleeve 116 rearward, so that the end face 116a of inner sleeve 116 is moved rearward and the front end of the instrument will have the shape determined by the end face 110b of sheath 110 (see FIG. 3). As has been mentioned above, end face 110b of the sheath has an inclined profile which corresponds to an angle of inclination of the lens of the cystoscope for lateral observation inside the urinary bladder.

After the preliminary cystoscopy is completed, the instrument is shifted rearward to the prostatic part of the urethra so that balloon 114 is aligned with the rear part of the prostatic portion of the urethra directly in front of the external urethral sphincter (not shown).

The instrument is then again converted into the resectoscope by shifting outer tubular portion 112 and inner sleeve 116 rearward, and the resectoscopic 90° optics is reinserted into the optical guide tube. A laser fiber (not shown) is then inserted.

The balloon is then inflated by injecting air, e.g., from an external source such as a syringe (not shown) via check valve 122. For this purpose, the syringe is pressed against valve element 124 and spring 128, so that air can pass through opening 126. The inflation of the balloon moves the enlarged prostatic lobes apart, thus drastically improving conditions for the observation of the operation site. If necessary, the outer tubular portion with balloon 114 can be slightly moved back and forth to further improve the observation conditions. If necessary, this additional movement may be used to discontinue bleeding in the operation site.

In the case of FIG. 3, disposable balloon 214, 215 is replaced similar to the embodiment of FIG. 1.

Figure 4:
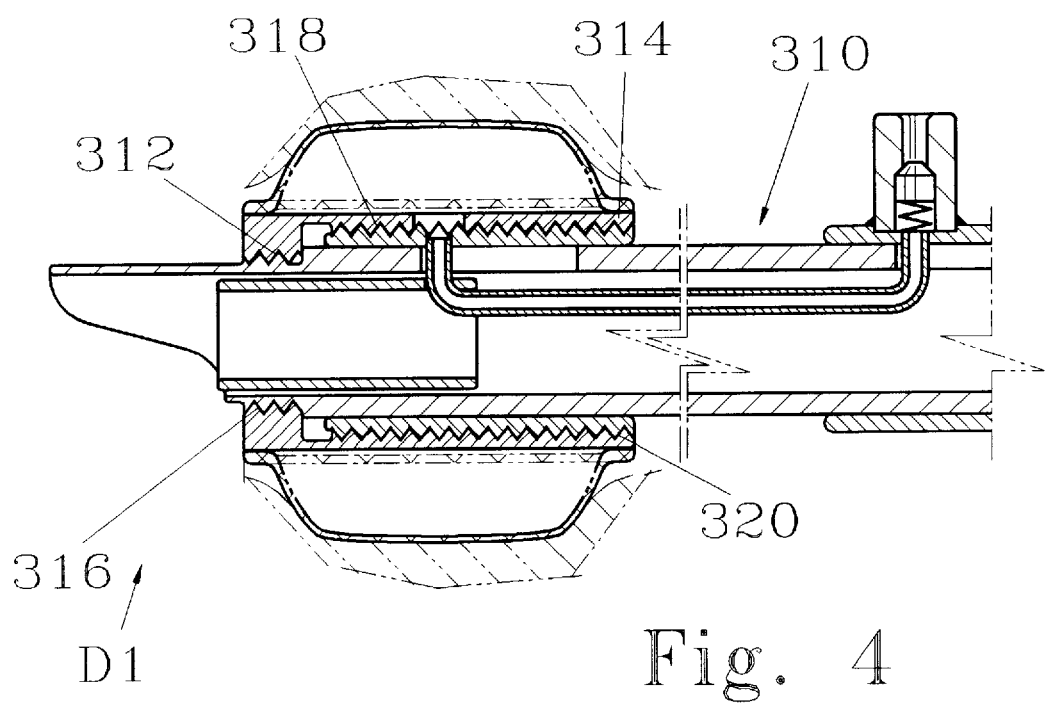
FIG. 4 is a fragmental view of the distal portion of a modified cystoscope of FIG. 3 which is provided with an additional lock thread on the distal end of the tubular sheath.

The embodiment of FIG. 4 is identical to the embodiment of FIG. 3 and differs by the provision of an outer thread 312 on the distal end D1 of sheath 310. On the other hand, balloon support sleeve 314 has a mating inner thread 316 which is screwed on thread 312. It is understood that threads 312, 316 have the same pitch as threads 318, 320 of balloon support sleeve 314 and sheath 310, respectively.

Provision of two threads on the balloon and the sheath ensures fixation of the balloon after engagement of the second pair of threads. In this embodiment, the balloon is connected to the cystoscope only after conversion thereof into a resectoscope by shifting the inner sleeve forward into a position shown in FIG. 2.

Thus, the instrument is inserted once and can be used both for observation and operation by shifting the inner sleeve forward or backward, thus converting the instrument into a resectoscope or a cystoscope. At the same, time, by supplying air into the balloon via the air-feed tube, which also function as a pusher for the sliding part of the instrument, it is possible to inflate the balloon and thus to move the prostate lobes apart and to improve observation conditions in the operation site.

It has been shown that the cystoscope of the invention fulfills functions of a cystoscope and a resectoscope which allows observation of the urinary bladder and of the prostatic part of the urethra, as well as the performance of prostatectomy itself with one insertion of the instrument into the patient's body. The instrument of the aforementioned type is capable of moving the prostate lobes apart and thus improving observation conditions for prostatectomy.

Although the invention has been shown and described with reference to specific examples, it is understood that these examples should not be construed as limiting the scope of the invention, and many other modifications are possible. For example, balloon 14 can be inflated by a resilient bulb attached to check valve 22. The instrument may be used for guiding means other than laser fiber or for supplying liquids other than a washing liquid. The air-feed tube may have different configuration and arrangement. The balloon can be attached to the outer tubular portion by adhesive. The instrument of the invention may find application not only in urology but in other endoscopical treatment or operation procedures, e.g., for spreading apart different organs in other body cavities. Therefore the scope of the invention is defined not by the examples given but by the patent claims and their legal equivalents.

We claim:

1. A cystoscope comprising:
    a main portion;
    a sheath portion insertable into the urethra of a patient and connected to said main portion, said sheath portion having a distal end and a proximal end, said sheath portion having an axial direction;
    an inflatable balloon attached to said distal end of said sheath portion; and means in said sheath portion for supplying a fluid to said balloon;
    said balloon having means for connecting to and disconnecting from said distal end of said sheath portion, and said means for supplying a fluid to said balloon comprising a check valve installed on said proximal end of said sheath and a tube that extends within said sheath portion in said axial direction between said check valve and said balloon.

2. The cystoscope of claim 1, further including a slider slidingly installed on said proximal end of said sheath portion; said means for supplying a fluid to said balloon comprising a check valve installed in said slider and a tube connecting said balloon to said check valve.

3. The cystoscope of claim 2, wherein said balloon having means for connecting to and disconnecting from said distal end of said sheath portion.

4. The cystoscope of claim 3, wherein said means for connecting and disconnecting comprises a male thread on said distal end of said sheath portion and a balloon support having a female thread engageable with said male thread, said balloon being sealingly attached to said balloon support, said balloon support having an opening which communicates with said tube when said balloon support is screwed onto said male thread.

5. The cystoscope of claim 4, further including means for converting said cystoscope into a resectoscope, said sheath portion having an end face of said distal end which has a cut out made in said axial direction and is inclined at an acute angle to said axial direction, said means for converting comprising:
    an outer sleeve portion slidingly installed on said distal end of said sheath portion;
    an inner sleeve portion slidingly inserted into said sheath portion and having an end face on the side of said distal end which is substantially perpendicular to said axial direction;
    said outer sleeve portion and said inner sleeve portion being connected for joint movement by said tube, said conversion being performed by shifting said outer sleeve and said inner sleeve forward toward said distal end of said sheath.

6. The cystoscope of claim 5, wherein said distal end of said sheath portion has an outer thread and wherein said balloon support has a second thread engageable with said thread on said distal end of said sheath.

* * * * *